US006188050B1

(12) United States Patent
Duffer et al.

(10) Patent No.: US 6,188,050 B1
(45) Date of Patent: Feb. 13, 2001

(54) SYSTEM AND METHOD FOR CONTROLLING PROCESS TEMPERATURES FOR A SEMI-CONDUCTOR WAFER

(75) Inventors: Charles E. Duffer; Jorge J. Alcoz, both of San Antonio, TX (US)

(73) Assignee: Karta Technologies, Inc., San Antonio, TX (US)

(*) Notice: Under 35 U.S.C. 154(b), the term of this patent shall be extended for 0 days.

(21) Appl. No.: 09/456,602

(22) Filed: Dec. 8, 1999

Related U.S. Application Data

(60) Provisional application No. 60/126,266, filed on Mar. 25, 1999.

(51) Int. Cl.[7] .................................................. H05B 1/02
(52) U.S. Cl. .................... 219/497; 219/502; 219/494; 392/416; 374/117; 438/715
(58) Field of Search .......................... 219/497, 502, 219/501, 494; 392/416; 73/597, 644, 119, 117; 372/92, 20; 438/715; 374/117, 119

(56) References Cited

U.S. PATENT DOCUMENTS

| 4,633,715 | 1/1987 | Monchalin . |
| 4,650,346 | * 3/1987 | Tehon .................................. 374/117 |

(List continued on next page.)

OTHER PUBLICATIONS

"Process Control and Sensors for Manufacturing", SPIE-The International Society for Optical Engineering, Richard H. Bossi and David M. Pepper, Mar. 31–Apr. 1, 1998, San Antonio, Texas.

"Noncontact Detection of Ultrasound with Rugged Fiber–Optic Interferometer", 1996 IEEE Ultrasonics Symposium, J.J. Alcoz, C.E. Duffer, S. Nair, vol. 1, 96CH35993, ISSN: 1051–01117.

"A Lamb Wave Temperature Sensor for Semiconductor Wafer Processing" Yichi Lu, Mary V. Moore, Doug T. Queheillalt, and Haydn N.G. Wadley, Review of Progress in Quantitative Nondestructive Evaluation, vol. 13, pp. 509–516.

"In situ Simultaneous Measurement of Temperature and Thin Film Thickness with Ultrasonic Techniques", J. PEI, B.T. Khuri–Yakub, F.L. Degertekin, B.V. Honeln, P.E. Stanke and Krishna C. Saraswat.

"Temperature Measurement in Rapid Thermal Processing Using Acoustic Techniques", Y.J. Lee, B.T. Khuri–Yakub, and K.C. Saraswat, Stanford University, Jan. 10, 1994.

*Primary Examiner*—Mark Paschall
(74) *Attorney, Agent, or Firm*—Jenkens & Gilchrist A Professional Corporation (57) ABSTRACT

A system for controlling process temperatures for semiconductor wafers comprises a heater to heat the wafer, an element to generate a plurality of ultrasonic vibrations in the wafer, a Sagnac interferometer adapted to sense the ultrasonic vibrations and generate a wafer temperature signal responsive thereto, a system to calculate the wafer temperature on the basis of the generated wafer temperature signal, and a control element the wafer heater on the basis of the calculated wafer temperature. A method for controlling process temperatures for semi-conductor wafers comprises the steps of heating the wafer, generating a plurality of ultrasonic vibrations in the wafer, sensing the ultrasonic vibrations with a Sagnac interferometer, generating the wafer temperature signal in response to sensing the ultrasonic vibrations with the Sagnac interferometer, calculating the wafer temperature on the basis of the generated wafer temperature signal, and controlling the heat applied to the wafer on the basis of the calculated wafer temperature.

20 Claims, 10 Drawing Sheets

U.S. PATENT DOCUMENTS

| | | |
|---|---|---|
| 4,979,134 | 12/1990 | Arima et al. . |
| 5,080,491 | 1/1992 | Monchalin et al. . |
| 5,098,198 | 3/1992 | Nuhman et al. . |
| 5,229,832 | 7/1993 | Gaynor . |
| 5,402,235 | 3/1995 | Monchalin . |
| 5,404,224 | 4/1995 | Kotidis et al. . |
| 5,469,742 | 11/1995 | Lee et al. . |
| 5,585,921 | 12/1996 | Peppet et al. . |
| 5,604,592 | 2/1997 | Kotidis et al. . |
| 5,608,166 | 3/1997 | Monchalin et al. . |
| 5,636,181 | 6/1997 | Duggal . |
| 5,638,396 | 6/1997 | Klimek . |
| 5,680,212 | 10/1997 | Blouin et al. . |
| 5,684,592 | 11/1997 | Mitchell et al. . |
| 5,718,231 | 2/1998 | Dewhurst et al. . |
| 5,732,046 | 3/1998 | O'Donnell et al. . |
| 5,996,415 * | 12/1999 | Stanke et al. .......................... 73/597 |
| 6,026,688 * | 2/2000 | Khuri-Yakub et al. ................ 73/597 |

* cited by examiner

SYSTEM AND METHOD FOR CONTROLLING PROCESS TEMPERATURES FOR A SEMI-CONDUCTOR WAFER

BACKGROUND OF THE INVENTION

This application claims the benefit under Title 35 United States Code §119(e) of U.S. Provisional Application No. 60/126,266, filed Mar. 25, 1999.

FIELD OF THE INVENTION

This invention relates generally to apparatus and methods which make use of laser-based ultrasonics, and more particularly, to methods and apparatus which incorporate laser-based ultrasonic signals to effect process control.

BACKGROUND OF THE INVENTION

The production of semiconductor wafers is a multibillion dollar industry, which feeds an even larger manufacturing sector based on consumer electronics. This rapidly growing sector places an ever-increasing demand on semiconductor production. Thus, even small improvements in semiconductor manufacturing process control can have a large impact on the economic viability of companies, products, and entire industries.

A critical factor in all semiconductor production processes is improved control of production processing parameters, particularly temperature. The driving force for better process control is the need to reduce integrated circuit feature size. Unfortunately, reduced feature size translates directly into less tolerance for errors, and the need for finer control over the entire production process.

For example, there is a dramatic dependence on maintaining a specified process temperature to ensure uniform deposition of polysilicon on a semiconductor wafer. At a Silane partial pressure of 10 Pascals, the deposition rate changes by over 18 Angstroms per minute for a 1° C. variance in processing temperature, which equates to about a 3% to about 20% change in the total deposition layer thickness each minute, over temperature. Other processes, such as Molecular Beam Epitaxy (MBE), chemical vapor deposition (CVD) and thermal annealing have even greater temperature dependence. All such processes stand to benefit from improved temperature control, as small variations in temperature can change the quality and functional properties of the wafers. This is even more important as wafer sizes increase, since, for example a 300-mm diameter wafer should be able to provide up to 2.5 times more chips than the 200-mm wafer.

Current methods for measuring temperature during semiconductor processing have several drawbacks. For example, thermocouples are fairly accurate, but are also invasive to the process. They cause Acool @ spots at the contact point and can only provide information at that point. For those processes where the gas environment composition is critical, thermocouples may also introduce contamination and oxidation problems.

Optical pyrometry provides a noncontact solution to this problem, but is hindered by changes that occur in the index of refraction, transmissivity of windows, and the emissivity of the wafer during the process. Stray radiation from wafer heating lamps also influences results, as does the inability to accurately know the emissivity for any particular wafer. Dual-wavelength pyrometer systems have been attempted as a way of obtaining emissivity-independence, but introduce other difficulties, such as requirements for distance calibration, and proportional emissivity throughout the measurement temperature range.

Laser ultrasonics (LU) to measure wafer temperature has been investigated for several years, but has not yet been demonstrated to accomplish industrial goals in a practical fashion. Ultrasound in the wafer is generated by relying on a basic thermoelastic mechanism in which the laser beam penetrates a short distance into the wafer before being completely absorbed. The light intensity must change very rapidly, generally in the form of a brief pulse. This raises the temperature of the penetrated volume of material before heat can escape, causing expansion of the surrounding medium and creating an acoustic pulse. Most of the stress applied to the wafer is in the radial directions on the surface plane, and thus LU is an efficient generator of surface waves, or guided waves. If the power of the laser is increased, the wafer surface begins to melt, and ultimately, the vaporization point is reached if even more power is applied.

The frequency spectrum of wafer-generated ultrasound is related to the temporal modulation of the laser. In principle, a laser beam could be modulated sinusoidally at the desired ultrasonic frequency, generating single tone ultrasound. In practice, a large average laser power would be needed to obtain significant ultrasound amplitudes, and the wafer under inspection would be heated appreciably. Instead, almost all laser-ultrasonics work has used pulsed lasers, which offer high peak intensities but low average powers. The ultrasound generated is intrinsically broadband. Pulses between 1 and 50 nsec long are used to obtain ultrasound peak amplitudes in a frequency range of about 0.5 and 25 MHZ. Even with pulses of this duration, the generated ultrasound ranges from DC to about 100 MHZ.

Lamb waves are guided acoustic waves that travel between two free boundaries. Their existence depends on the product of the acoustic frequencies and the thickness of the material. Thus, Lamb waves are well suited to investigate the behavior of plates and plate-like structures, such as wafers. The acoustic energy in Lamb waves may propagate in one or more modes (infinite modes are possible). However only the fundamental (zereoth order) symmetric and anti-symmetric modes can propagate for all frequency-thickness combinations. Furthermore, the fundamental anti-symmetric ($A_0$) mode has much greater amplitude than the symmetric mode, and is thus more effectively measured and analyzed. Therefore, its use is preferred. The phase velocity of the Lamb wave depends on the combination of frequency, thickness, and the material properties of the plate. Variations of either thickness or material properties cause distinct phase velocity changes. The theory for deriving the dispersion relationships is illustrated in *Rayleigh and Lamb Waves* (Plenum, N.Y., 1967), by I. A. Viktorov, incorporated herein by reference in its entirety.

It has been determined that lasers can efficiently generate the lowest order anti-symmetric ($A_0$) mode of the Lamb wave, which is sensitive to changes in temperature and to the wafer film coating thickness. In fact, using various techniques, experimental measurement accuracies of about ±0.15° C. have been obtained using the changes in velocity of the $A_0$ Lamb wave mode. The governing equation for the anti-symmetric Lamb wave mode is presented by a number of well-recognized sources. A basic form of the equation is given below:

$$\frac{\operatorname{Tan}(qh)}{\operatorname{Tan}(ph)} = \frac{(q^2 - k_a^2)^2}{4\Delta_a^2 pq}$$

where $$p^2 = \left(\frac{\omega}{c_L}\right)^2 - k_a^2 \text{ and } q^2 = \left(\frac{\omega}{c_T}\right)^2 - k_a^2$$

such that $\omega$ is the angular frequency, $k_a$ is the wave number of the $A_0$ Lamb mode, $c_L$ is the longitudinal wave speed, $c_T$ is the transverse wave speed, and $h$ is the half thickness. Variations of this equation can be derived for propagation in specific directions that coincide with the cubic crystal structure of the semiconductor materials.

Different optical detection schemes exist to measure temperature using ultrasound, including the fiber Fizeau interferometer, and the Aknife-edge @ detector. A fiber Fizeau interferometer is one of the simplest, most sensitive, ultrasonic interferometric detectors available. In this detector configuration, light reflected by the monitored surface interferes with light reflected at an intermediate point, typically at the exit surface of the illuminating fiber or lens. Thus, the amplitude of the detected light is modulated by changes in the distance between the optics and the wafer.

The Fizeau interferometer is in essence a single-pass Fabry-Perot interferometer wherein the cavity is formed by an air gap between the probe and the surface. Its main drawback is that this gap has to be maintained at an odd number of quarter optical wavelengths. Thus, environments with mechanical vibrations mandate some sort of position feedback to maintain this so called Aquadrature @ condition.

The Fizeau works well at room temperature, detecting laser-generated Lamb waves in wafers with good signal-to-noise ratio. However, when used in a furnace environment, the return signal is severely degraded. This can be attributed to changes in the cavity effective optical length due to air currents, and expansion of the wafer holder. Further, while the Fizeau enables ultrasonic inspections without contact, general optical methods are employed to couple ultrasound into the component, and to detect the corresponding (temperature-dependent) ultrasonic echoes. Thus stability issues continue to exist, as well as the expense involved in constructing a system with a minimum of expensive optical components.

The knife-edge detector is also capable of making basic temperature measurements, after a fashion. However, this instrument is based on the principle of specular reflection, which requires a highly polished and nearly optically-flat surface to ensure accurate results.

Other temperature measurement approaches have also been attempted in the processing of semiconductor wafers, using laser-generated ultrasound, but none has proved to provide stable, accurate, and inexpensive process control capability. These include interferometric-based materials analysis systems that employ shaped laser beams, and signal processing techniques to compensate for inherent instabilities of the diode lasers used in such systems. Matched-filter processing techniques are also employed to analyze Lamb L-waves generated within silicone wafer targets; however, such a system is cumbersome, requires a special optical bench to support it, and includes many expensive and critically-constructed optical components.

Therefore, what is needed is a laser-generated ultrasound process control system for semiconductor wafers which is inexpensive, rugged, and relatively insensitive to heat, stand-off distance, and air currents which may result from the process itself

SUMMARY OF THE INVENTION

The invention includes a system for controlling process temperatures for a semiconductor wafer comprising a means to heat the wafer, which may be a resistance heater or light bulb; a means for generating a plurality of ultrasonic vibrations in the wafer; which may be a laser or other source of monochromatic light; a Sagnac or polarimetric Sagnac interferometer; which is adapted to sense the ultrasonic vibrations and generate a signal which is indicative of the wafer temperature; and responsive to the sensed signal, a means to calculate the wafer temperature on the basis of the signal (which may be a digital signal processor, or a general-purpose embedded microprocessor); and a means to control the wafer heater based on the determined wafer temperature, such as a Proportional, Integral, Derivative (PID) controller.

The invention also includes a method for controlling process temperatures for a semiconductor wafer, comprising the steps of heating the wafer, generating a plurality of ultrasonic vibrations in the wafer, sensing the vibrations with a Sagnac or polarimetric Sagnac interferometer, generating a wafer temperature signal in response to the vibrations, calculating the wafer temperature on the basis of the wafer temperature signal provided by the interferometer, and controlling the heat applied to the wafer on the basis of the calculated wafer temperature, using a PID controller, for example. As noted for the system above, the heating step may be accomplished using a resistance heater or light bulbs.

The ultrasonic vibrations are typically induced as Lamb waves in the wafer by using a laser or other source of monochromatic light. The wafer temperature signal is generated by sensing the ultrasonic vibrations, and applying digital signal processing to isolate the phase velocity of Lamb waves generated within the wafer. The calculating and controlling steps may be effected with an embedded microprocessor or digital signal processor, such that the wafer temperature is calculated on the basis of the generated wafer temperature signal (i.e., the phase velocity of the Lamb waves), and control signals are applied to the wafer heater on the basis of the calculated temperature.

The system and method for controlling process temperatures using a polarimetric Sagnac interferometer offers several advantages, including the provision of a system which is rugged, relatively insensitive to heat, stable, inexpensive, and practical for use in industrial environments.

BRIEF DESCRIPTION OF THE DRAWINGS

A more complete understanding of the structure and operation of the present invention may be had by reference to the following detailed description when taken in conjunction with the accompanying drawings, wherein.

DETAILED DESCRIPTION OF THE INVENTION

Figure 1:
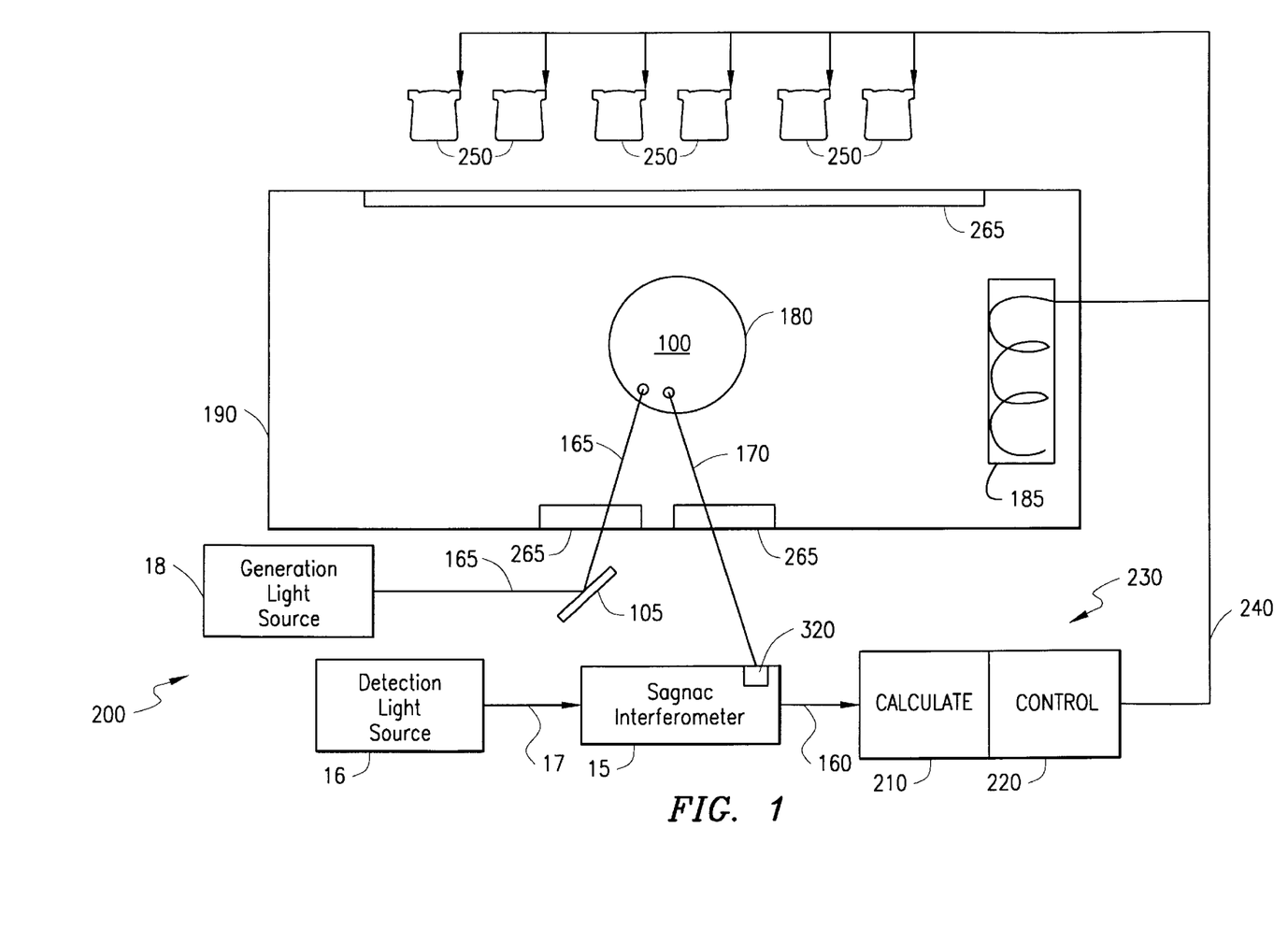
FIG. 1 is a block diagram of the process control system for semiconductor wafers of the present invention.

Reference is now made to FIG. 1, wherein is shown a block diagram of the process control system of the present invention. The system for controlling process temperatures for a semi-conductor wafer, or control system (200), comprises a furnace (190), or other means to heat the wafer (180), a generation light source (18), or other means for generating a plurality of ultrasonic vibrations in the wafer (180), a Sagnac interferometer (15) adapted to sense the plurality of ultrasonic vibrations and generate a wafer temperature signal in response thereto, a calculation means (210), such as a microprocessor or personal computer, to calculate the wafer temperature on the basis of the generated wafer temperature signal, and a control means (220), such as a microprocessor or personal computer, to control the wafer heating means (190) on the basis of the calculated wafer temperature. The calculation means (210) and control means (220) may be combined into a single entity, such as a computer (230). An embedded microprocessor, digital signal processor, or personal computer may be used as the computer (230).

The means to heat the wafer (180) may be a resistance heater (185) contained in the furnace (190). The means to the heat the wafer (180) may also be one or more light bulbs (250). Optical access to the wafer (180) is achieved using open ports, or a series of sapphire or fused silica windows (265). The generation light source (18) is typically a laser or other source of of coherent light capable of producing power densities on the order of 3 milliJoules with a pulse length of less than 50 nsec. This translates to a power density at the surface of the wafer (180) on the order of 1 MW/cm$^2$ for thermoelastic generation, and 10 MW/cm$^2$ for ablative generation. The inspection beam (165) emanating from the generation light source (18) may be steered by way of a generation mirror (105) onto the wafer surface (100).

After ultrasonic vibrations are set up in the wafer (180), the Sagnac interferometer (15), using a source of monochromatic light (17), such as a stable continuous wave or long pulse laser detection light source (16), is used to sense the ultrasound perturbations on the wafer surface (100) by means of the reflected beam (170). These ultrasonic perturbations on the wafer surface (100) are proportional to the temperature of the wafer surface (100), and the resulting signal, which is an ultrasound modulated wafer temperature signal (160), is passed on to the calculation means (210) to produce a temperature reading. Once the wafer temperature is calculated on the basis of the sensed wafer temperature signal (i.e., the reflected beam (170)), the heat applied to the wafer (180) may be controlled by the control means (220) using the heater control signal (240) applied to a series of lamp bulbs, or other heater means (250).

Thus, the method for controlling process temperatures for a semi-conductor wafer embodied in the present invention comprises the steps of heating the wafer (180), generating a plurality of ultrasonic vibrations in the wafer (180), sensing the plurality of ultrasonic vibrations with a Sagnac interferometer (15), generating a wafer temperature signal (160) in response to the plurality of ultrasonic vibrations, calculating the wafer temperature on the basis of sensed wafer temperature signal (160), and controlling the heat applied to the wafer (180) on the basis of the calculated wafer temperature. As mentioned above, the method of controlling process temperatures may be carried out using a resistance heater (185) or light bulbs during the heating step. The step of generating a plurality of ultrasonic vibrations may include the step of directing one or more sources of light (multiple sources will typically be separated in space or time, such as occurs with a phased or linear array of monochromatic light sources), including laser beams or other monochromatic light, to the surface of the wafer (180). The step of sensing the plurality of ultrasonic vibrations with a Sagnac interferometer may include the step of using a polarimetric Sagnac interferometer. The step of calculating the wafer temperature on the basis of the sensed wafer temperature signal (160) may include the step of Lamb wave phase velocity determination within the wafer, and may be carried out using an embedded microprocessor, a digital signal processor, or a personal computer. The step of controlling the heat applied to the wafer on the basis of the calculated wafer temperature may also be carried out using a Proportional, Integral, Derivative (PID) controller, an embedded microprocessor, a digital processor, or a personal computer.

To heat and maintain wafers (180) at a constant temperature, a current-control furnace, fitted with several port holes, such as a Lindberg Model No. 55322 may be used. The nominal maximum temperature of the furnace is typically about 1200° C. The furnace controller, or control means (220) may be a Eurotherm 81AP digital controller with set-point programming. Fused silica or sapphire window covers for the port holes may be used to limit drafts due to conduction of hot air over the wafers (180). It is generally a desirable practice to use a larger port hole for detection (i.e., passage of the reflective beam (170) out of the furnace (190)) so that the detector probe of the Sagnac interferometer (15) can be scanned over the wafer surface (100). Typical scanning assemblies include a linear translation stage with micrometer movement capability, to allow precise propositioning in increments of 1 mm steps.

The detection light source (16) is usually selected so as to provide stable interferometric detection, using a continuous wave long pulse laser. The laser should not have a coherence length greater than the maximum path difference between the reference and sensing beams within the Sagnac interferometer (15).

Figure 2:
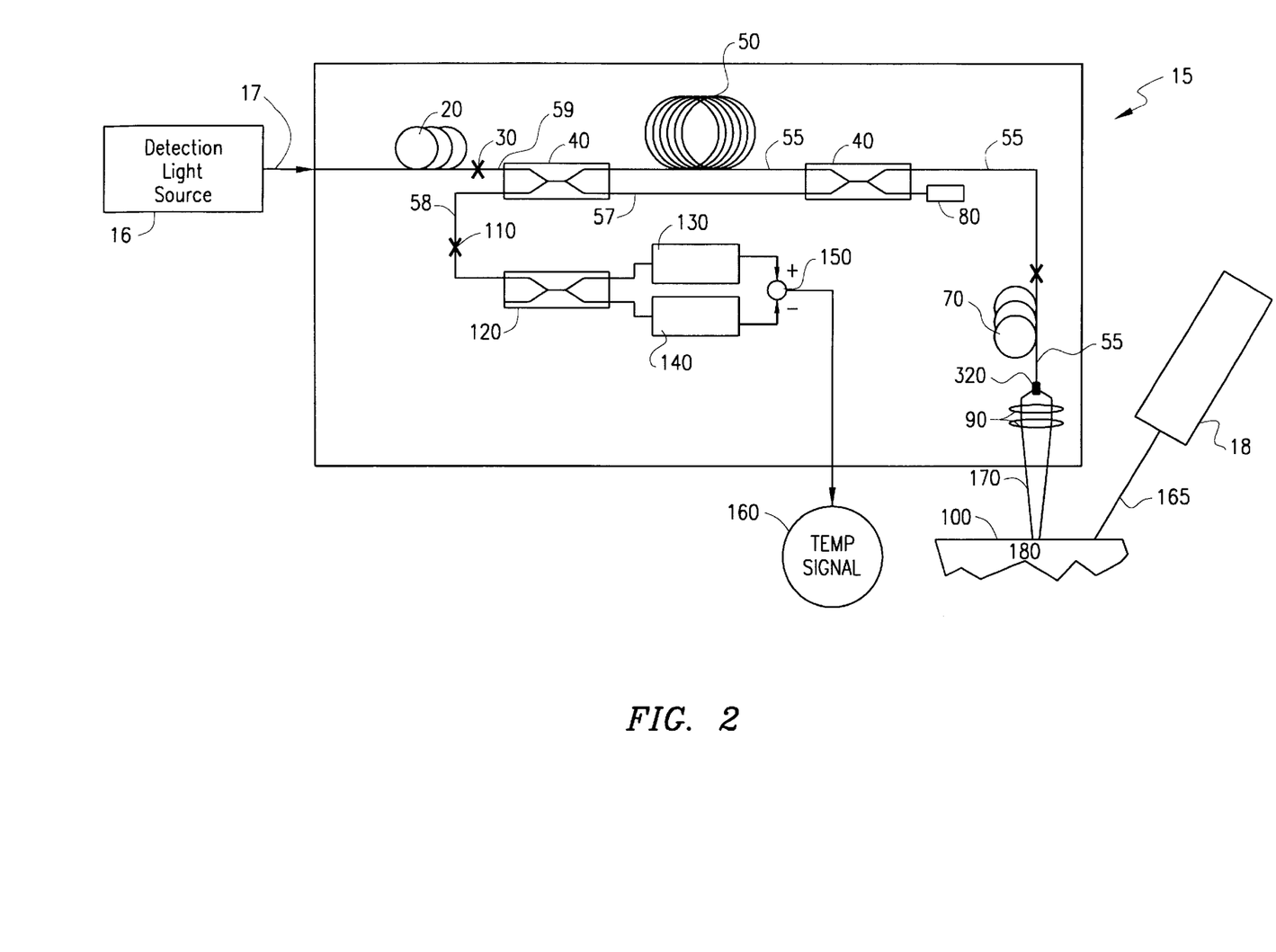
FIG. 2 is a block diagram of the polarimetric Sagnac Detection System as an element of the present invention.

Turning now to FIG. 2, the fiber-optic implementation of a polarimetric Sagnac interferometer (15) can be seen. Monochromatic light (17), or light which is spatially/temporally coherent, which means coherent within a distance of less than about 300 mm, or the distance of the shortest optical path length of the inteferometer, provided by the detection light source (16), which may be a laser diode or other source of light is passed into the polarization maintaining (PM) fiber (55) first polarization maintaining PM fiber input (30) after the polarization of the light is adjusted using the first fiber-polarization-controller (FPC) (20), which is a variable length of optical fiber (55) that can be physically manipulated, or stressed, to adjust the fiber polarization preference and provide a clean interference signal with a higher signal-to-noise ratio when adjusted to operate as a ¼ wave plate. The directional coupler (40) splits the light into two equal power counter-propagating beams. The first beam travels through a long length of PM fiber (55), comprising a delay loop (50), before reaching the first fiber-polarizing-beamsplitter (FPB) (60). Any light propagating along the fast mode of the PM fiber (55) delay loop (50) is coupled into a light dump (80), while the light propagating along the slow mode of the PM fiber (55) is sent toward a second FPC (70), focused onto the detector probe (320) from the lens assembly (90), and emerges to make contact with the wafer surface (100) of the wafer (180). Some of the reflected or backscattered light, comprising reflected beam (170), is then collected by the detector probe (320) from the lens assembly (90), and returned into the fiber (55). The FPC (70) is adjusted to operate as a quarter-wave plate, converting the slow-mode, linearly-polarized light into right-circular polarized light (an off-the-shelf ¼ wave plate may be substituted for the FPC (70)), and the reflected beam (170) is converted so as to propagate along the fast mode of the fiber (55). The FPB (60) directs the right-circular polarized light and fast-mode polarized light into the short arm (57) of the loop, so as to return it to the directional coupler (40). This completes the remaining portion of the clockwise light travel path.

Similarly, light entering the directional coupler (40) and passing onto the short arm (57) of the loop is split at the first FPB (60) into a slow-mode element, directed toward the light dump (80), and a fast-mode element, directed toward the second FPC (70). The second FPC (70) converts the fast-mode light to left-circular polarized light, focused onto the detector probe (320) from the lens assembly (90) onto the wafer surface (100). Again, part of the reflected or backscattered light is collected as reflected beam (170) by the detector probe (320) from the lens assembly (90) and coupled back into the fiber (55). The second FPC (70) converts the collected light (reflected beam) (170), which is right-circular polarized, into linearly polarized light for travel along the slow-mode of the fiber (55). The FPB (60) couples all of this light into the long arm of the loop, which contains the delay loop (50). The delayed propagating light finally reaches the directional coupler (40), completing the remaining portion of the counter-clockwise loop path.

One-half of the clockwise and counter-clockwise propagating light is sent by the directional coupler (40) into the output fiber (58), which is spliced to a second PM fiber input (110) so as to enter a second FPB (120). The axes at the splice, or second PM fiber input (110) are rotated 45° with respect to each other so as to produce interference between the clockwise and counter-clockwise modes, producing two orthogonally polarized modes separated by the second FPB (120) and each detected by a first and second photodetector (130) and (140), respectively. The interference signals passed on by the first and second photo detectors (130) and (140) are complementary, and can be electronically summed at the summing amplifier (150) to obtain a wafer temperature signal (160) modulated by the ultrasound present at the wafer surface (100).

The first FPC (20) is adjusted so that equal power is coupled at the first PM fiber input (30) into the slow and fast modes of travel so that the static phase difference between the modes when they interfere at the second PM fiber input (110) is 90°. Generally, when this condition is achieved, the light entering the PM fiber input (30) will not be circularly polarized (i.e., the fast and slow modes generated will not have a phase difference of 90°). The input and output of the Sagnac loop introduce phase shifts because the output fiber (58) and the input fiber (59) are not part of the path-matched Sagnac loop.

The directional coupler (40) sends half of the light of each counter-propagating beam towards the second PBS (120). A 45° splice at the second PM fiber input (110) forces these beams, which have orthogonal polarizations, to interfere. The second PBS (120) directs each interference beam to a separate photodetector, first and second photo detectors (130) and (140). The outputs of each detector (130) and (140) are 180° out-of-phase, and by subtracting them from each other the signal amplitude is doubled, while laser noise is eliminated.

As in any other single-path interferometer, the response is sinusoidal with respect to the phase difference. In order to work within the linear portion of the response, a 90° phase bias should be provided; in this case, the first FPC (20) acts as a ¼ waveplate outside the Sagnac loop to provide a passive bias. The first FPC (20), being variable, is able to compensate for the additional phase difference introduced by the birefringence of the output and input fibers (58) and (59), respectively.

A polarimetric Sagnac interferometer (15) has the substantial benefit of to relative insensitivity to outside perturbations. All of the components which form part of the Sagnac loop (i.e., the directional coupler (40), delay loop (50), the first FPB (60), light dump (80), second FBC (70), and fiber (55)), are intrinsically immune to reciprocal perturbations. At each specific point of the loop, the clockwise and counter-clockwise beams have identical polarization; birefringence or other polarization-dependent changes in the loop do not effect its output. As an additional means of stabilizing the operation of the system (200), the first FPC (20) may be replaced by a zero-order wave plate, and the input and output fibers (59) and (58) can be eliminated using direct connections to the directional coupler (40) and second FPB (120).

Figure 3:
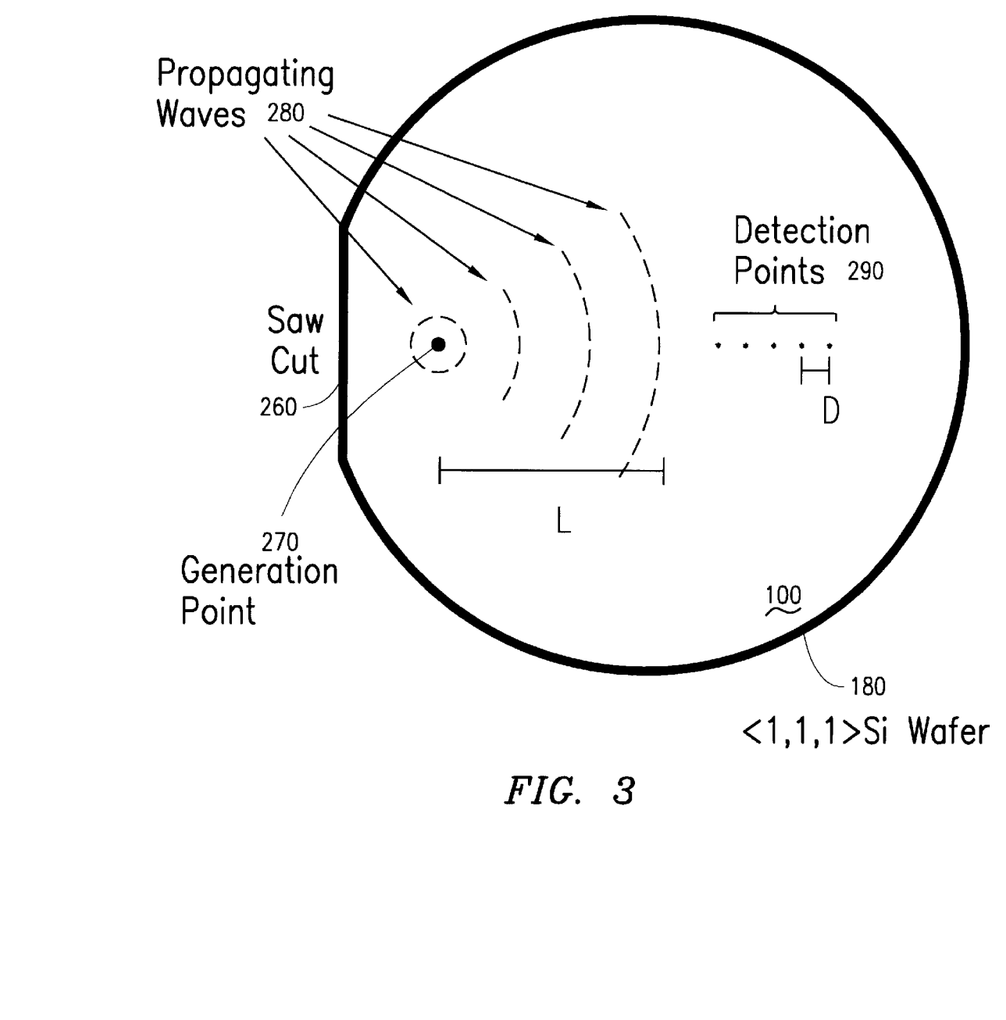
FIG. 3 illustrates a top-side view of single-source ultrasound generation in a semiconductor wafer.

Turning now to FIG. 3, a top-side view of single-source ultrasound generation in a semi-conductor wafer (180) can be seen. The wafer surface (100) is oriented according to the saw cut (260), such that the direction of propagation according to the distance L is in perpendicular alignment. The distance L is typically on the order of several millimeters, and most preferably, between about 10 mm and 100 mm.

The process of gathering temperature samples from the wafer surface (100) is typically accomplished by setting the furnace controller (220) to the desired temperature, and waiting for the temperature to settle at that point within approximately "0.5° C. Then, a plurality of ultrasonic vibrations in the wafer (180) are generated by activating the generation light source (18) so as to impact the wafer surface (100) at the generation point (170). The propagating ultrasound waves (280) expand from the generation point (270) along the distance L to reach one or more detection points (290) on the wafer surface (100). The Sagnac interferometer (15) is activated, using the detection light source (16) to sense the plurality of ultrasonic vibrations resulting from the propagating waves (280) and generating a wafer temperature signal (160) in response to the ultrasonic vibrations. The spacing D between the detection points (290) is typically on the order of one millimeter. A translation stage may be used to move the Sagnac detector lens assembly (90) along the distance L according to the spacing between the detection points (290). After sensing the plurality of ultrasonic vibrations with the Sagnac interferometer (15), and generating a wafer temperature signal (160) responsive thereto, the wafer (180) temperature can be calculated on the basis of the sensed wafer temperature signal (160). Finally, the heat applied to the wafer (180) can be controlled on the basis of the calculated wafer temperature. If the temperature sensed the wafer surface (100) is above that desired, then the furnace (190) resistance heater (185), or the heater means (250) can be deactivated. On the other hand, if the temperature is below that desired, the various means to heat the wafer (185) and (250) may be activated so as to raise the wafer surface (100) temperature to the desired level.

The principle of narrow band acoustic wave generation is based on the idea that an array of generation sources, including especially a phased array or linear array of monochromatic sources, can be set up to reinforce the acoustic amplitude of surface or plate guided waves in a particular direction of propagation, producing acoustic waves within a narrow frequency band. The separation between the generation sources is the primary influence on the frequency that is generated. A large array size (i.e. many sources) increases frequency reinforcement and produces a narrower bandwidth. For optimum narrow band generation, the peak frequency of the of the original broad-band signal obtained using single source generation should be tuned (by varying the laser beam width) to match the desired narrow band frequency. This process is discussed in *Ultrasonics*, vol. 29, pages 230–234 (1991), "Laser Generation of Antisymmetric Lamb waves in thin plates" by H. Nakano and S. Nagai and the *J. Acoust. Soc. Am.*, vol. 92(5), pages 2527–2531 (1992), "Laser generation of narrowband surface waves," by J. Huang, S. Krishnaswamy, and J. D. Achenbach, incorporated herein by reference in their entirety.

Several laser-based methods for generating narrow band ultrasound using array techniques exist. A properly oriented array of generation sources reinforces the acoustic amplitude in a particular direction of propagation and produce waves with a narrow frequency band. However, most known generation methods are sub-optimal, because the illuminated array of generation points on the wafer surface is not uniform with respect to energy distribution. This problem is magnified due to uneven distribution of the energy in the original laser beam.

Figure 4:
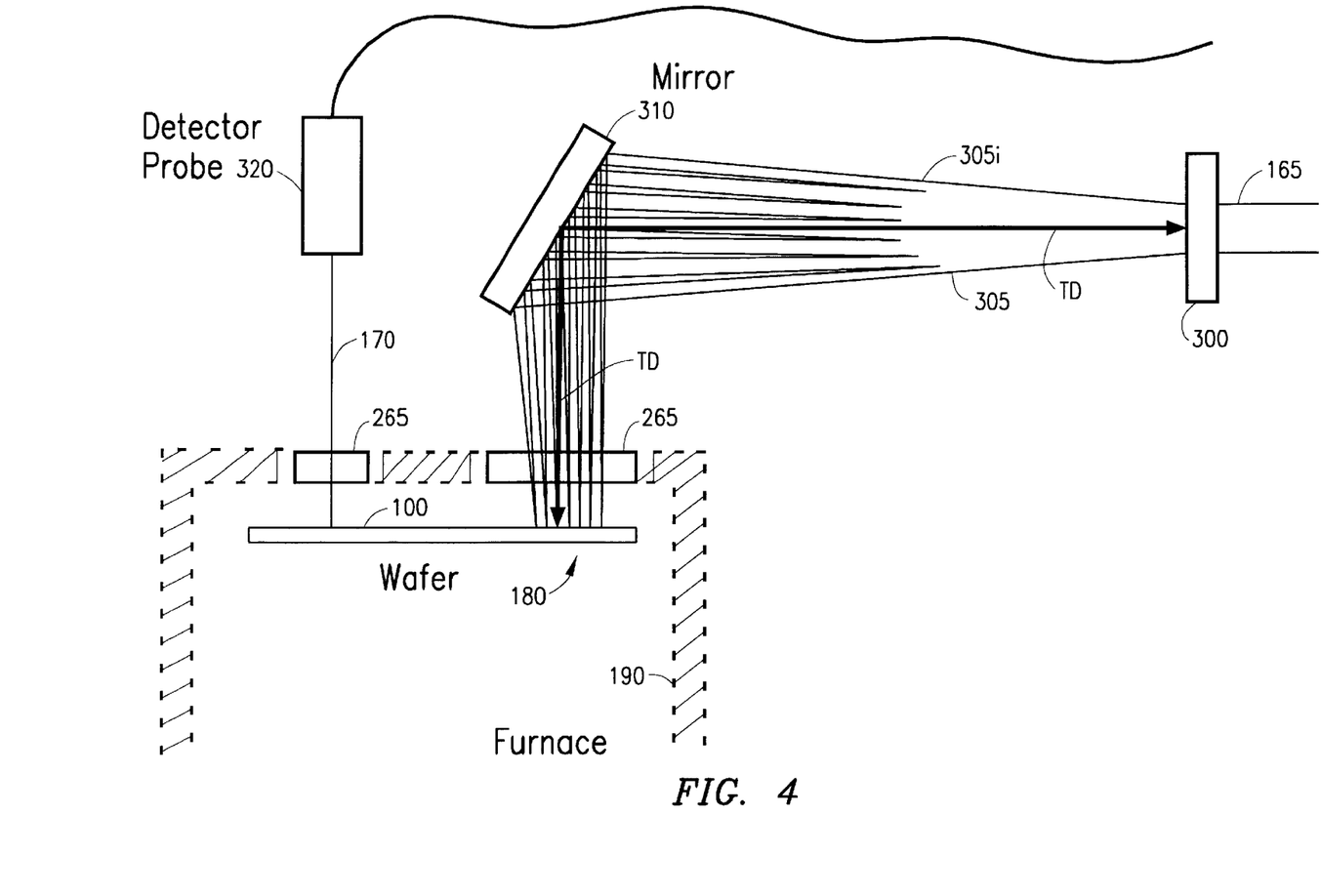
FIG. 4 illustrates a side-view of multiple-source ultrasound generation in a semiconductor wafer.

The best ultrasound vibration generation methods use a phase grating and cylindrical lens system to produce a linear array of monochromatic light sources; e.g. a binary optical element BOE (300) for multiple beam splitting, as shown in FIG. 4. High efficiency and uniform beam splitting make the BOE (300) a better choice than a phase grating. This technique reduces the generated ultrasound bandwidth, which simplifies the analysis and increases the signal-to-noise ratio (and thus, the accurate temperature sensing ability of the system (200)). In addition, the total laser input energy can be increased in accord with the number of beams in the generating array. Otherwise, the amount of energy is limited to that which can be nondestructively delivered in a single beam to the wafer surface (100).

As shown in FIG. 4, a BOE (300) can be employed to split the inspection beam (165) into a fan of beams (305) focused on the wafer, with equal power and equal spacing. By changing the distance between the BOE (300) and the wafer (180) the array spacing can be varied.

Figure 5:
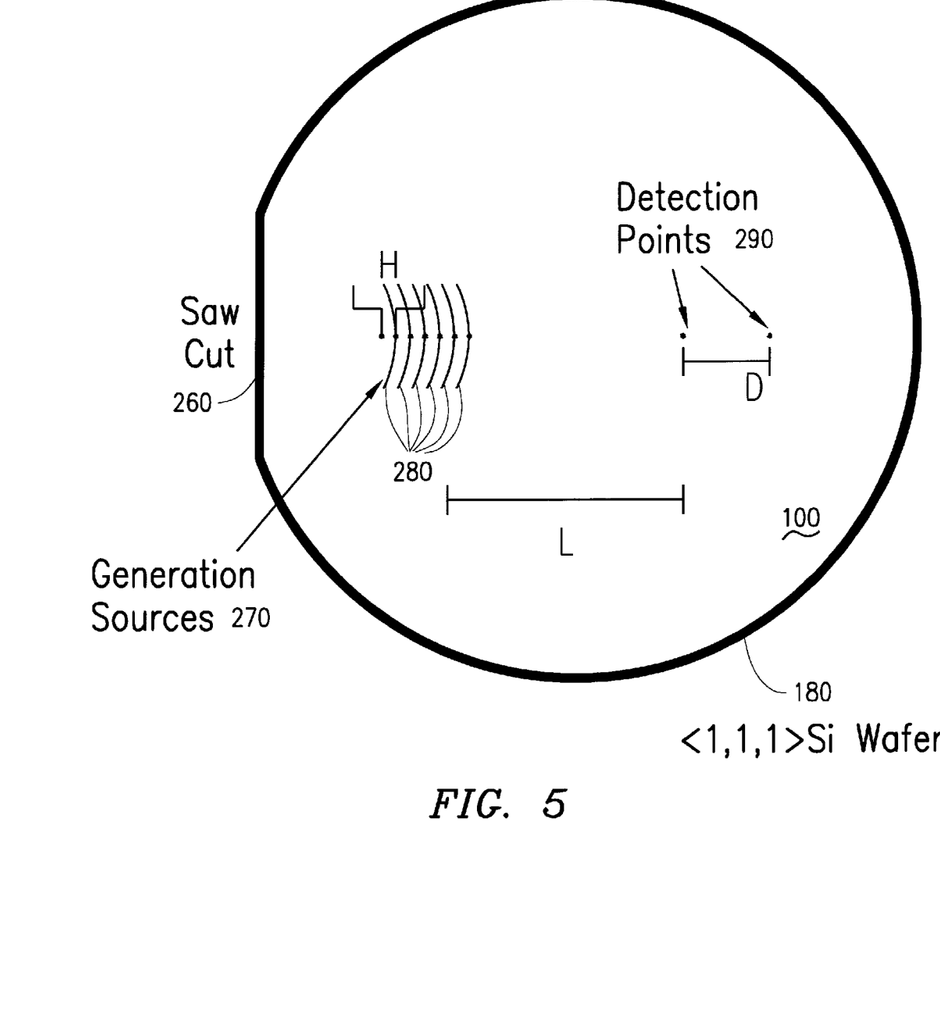
FIG. 5 illustrates a top-view of multiple-source ultrasound generation in a semiconductor wafer.

FIG. 5 illustrates a top view of multiple source ultrasound generation in a silicon wafer (180). As with single source generation, the ultrasonic wave (280) propagation distance, L, typically varies between about 10 mm to about 100 mm, and the propagation direction is aligned perpendicularly to the wafer saw cut (260). Generation is divided between multiple points, spaced by a distance H, controlled by changing the distance between the BOE (300) and the wafer (180). Sensing is performed at one point (290), or more points (290) separated by a distance D.

The method for controlling process temperatures to the present invention, using multiple source ultrasound generation such as a phased array, or linear array of monochromatic light sources, comprises the steps of adjusting the BOE (300) optical distance TD, which is the total distance from the BOE (300) to the wafer surface (100), as (optionally) intercepted by a mirror (310) to set the spacing of the generation point sources (270) so as to coincide with the ultrasonic wave length which is to be reinforced by the array. Source (270) spacing is equivalent to the desired wavelength, and related to the wave speed and frequency in the material by the formula:

$$(\text{delta}) \int_{spacing} = D_{wavelength} = C_{speed}/f_{frequency}$$

The wafer (180) is then heated, and a plurality of ultrasonic vibrations are generated in the wafer (180) due to the energy induced by the array of generation sources (270). The detector probe (320) is positioned so as to receive backscattered light, or the reflected beam (170) from one or more detection points (290) on the wafer surface (100). Typically, the lens assembly (90) will be interposed between the detector probe (320) and the window (265).

The plurality of resulting ultrasonic vibrations in the form of propagating waves (280) will be sensed at the detection points (290) using the Sagnac interferometer (15), and a wafer temperature signal (160) will be generated in response to sensing the ultrasonic vibrations. The temperature of the wafer (180) may then be calculated based on the characteristics of the generated wafer temperature signal (160), and the control means (220), such as a PID controller, may be applied to the heater means (250), which may include a resistance heater (185), to control the heat applied to the wafer (180) on the basis of the calculated wafer temperature.

Figure 6:
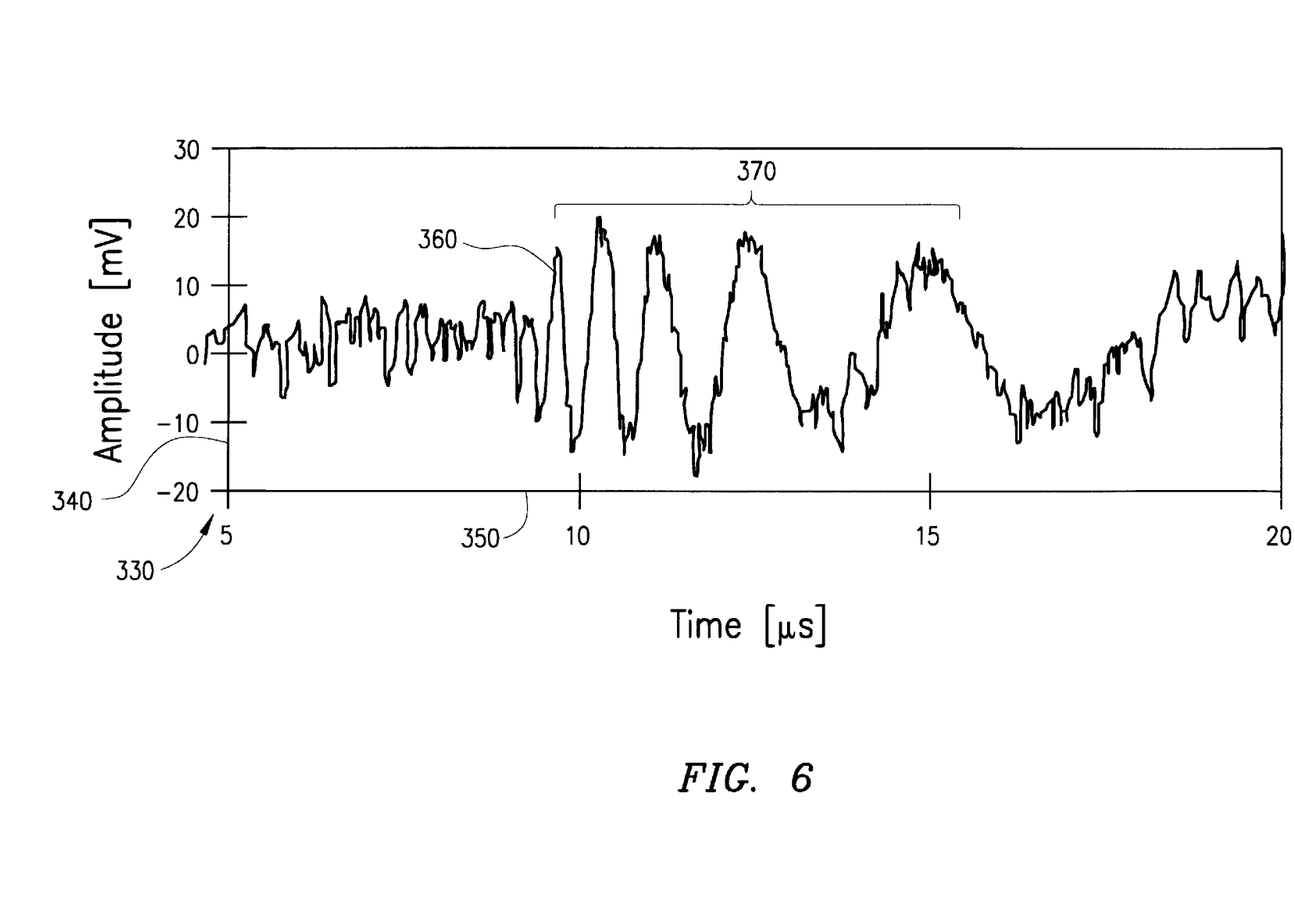
FIG. 6 illustrates a graph of ultrasound-generated Lamb waves as detected at 48 mm from the source generation point.

The polarimetric Sagnac interferometer (15) used within the system (200) has a periodic frequency response that decreases slowly apart from the resident frequency. Thus, large bandwith signals will be distorted. However, such response characteristics do not effect the time-of-flight algorithms necessary to determine the wafer temperature, which means the precision of the temperature readings is also not effected. For example, arbitrarily choosing the maximum response of the Sagnac interferometer (15) to occur at 3.75 MHz, provides a signal of approximately constant amplitude, as shown in FIG. 6. The Sagnac interferometer (15) frequency response does not effect the zero-crossing times of the signal, and therefore, timing information is maintained and the signal-to-noise ratio is enhanced.

Figure 7:
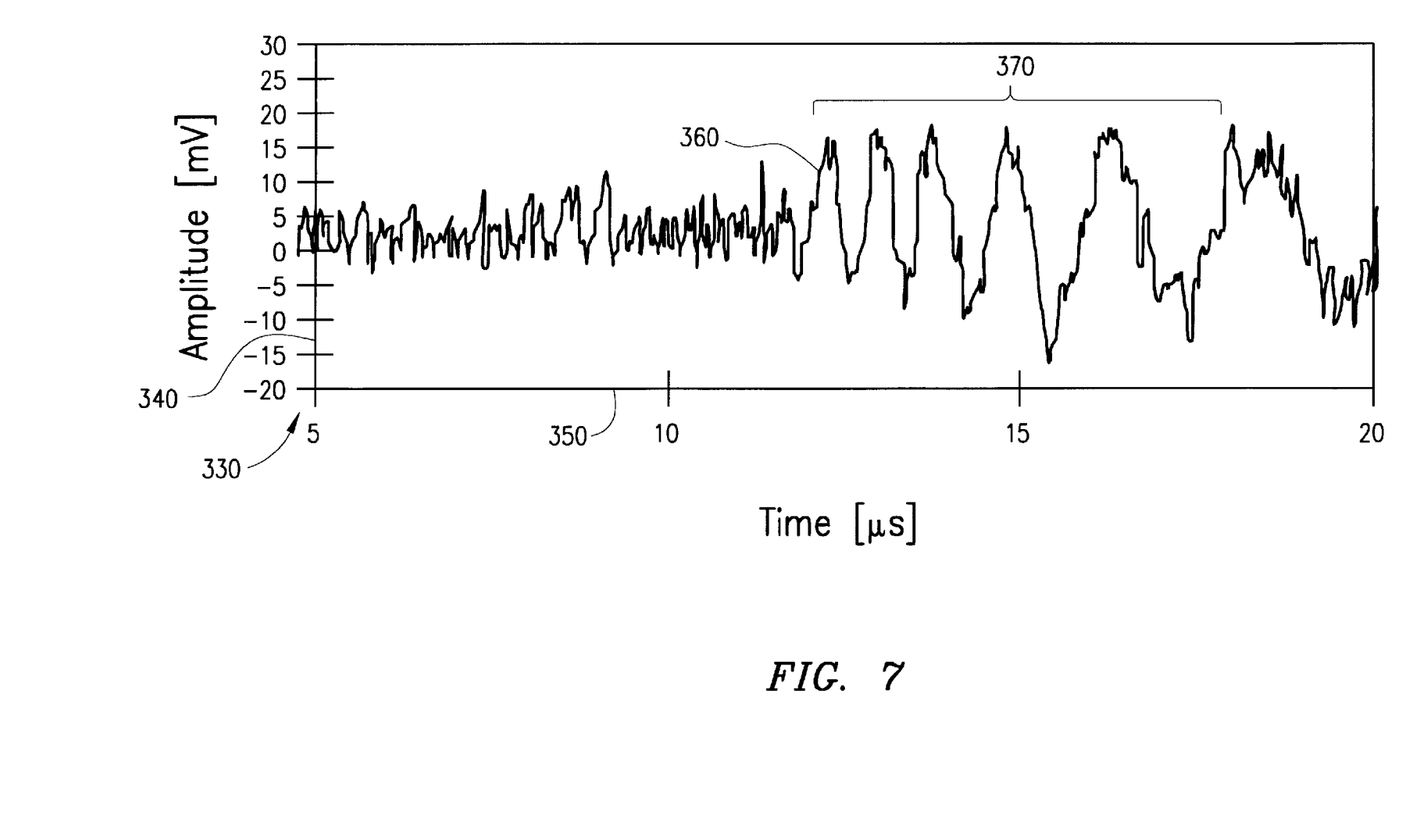
FIG. 7 illustrates a graph of ultrasound-generated Lamb waves as detected at 53 mm from the source generation point.

The fundamental anti-symmetric Lamb wave is dispersive in the wafer (180); i.e., different frequencies travel at different velocities. Such behavior makes the task of extracting temperature information more difficult. As seen in FIG. 6, the time history of the fundamental anti-symmetric Lamb mode wave can be seen after propagating a distance L equal to 48 mm from the generation point (270), as seen in the amplitude versus time graph (330). As shown in FIG. 6, the amplitude axis (340) is measured in terms of milliVolts and the time axis (350) is measured in terms of microseconds. The detected ultrasound (UT) wave (360) shows a series of dispersed peaks (370), representing the different frequencies traveling at various velocities within the wafer (180). FIG. 7 illustrates a graph of ultrasound-generated Lamb waves detected at distance L=53 mm from the source generation point (270). Comparing FIGS. 6 and 7, it can be seen that the dispersed peaks in FIG. 7 are farther apart in time than those in FIG. 6. That is, even though the waves have traveled only 5 mm farther, they have dispersed in time so as to be significant with respect to the frequency. Using typical nondispersive analysis, the time between peak correlation, or zero-crossings, is used to provide a measure of the wave velocity in the medium. In this case, such an analysis is not possible, and advanced signal processing is required.

Figure 8:
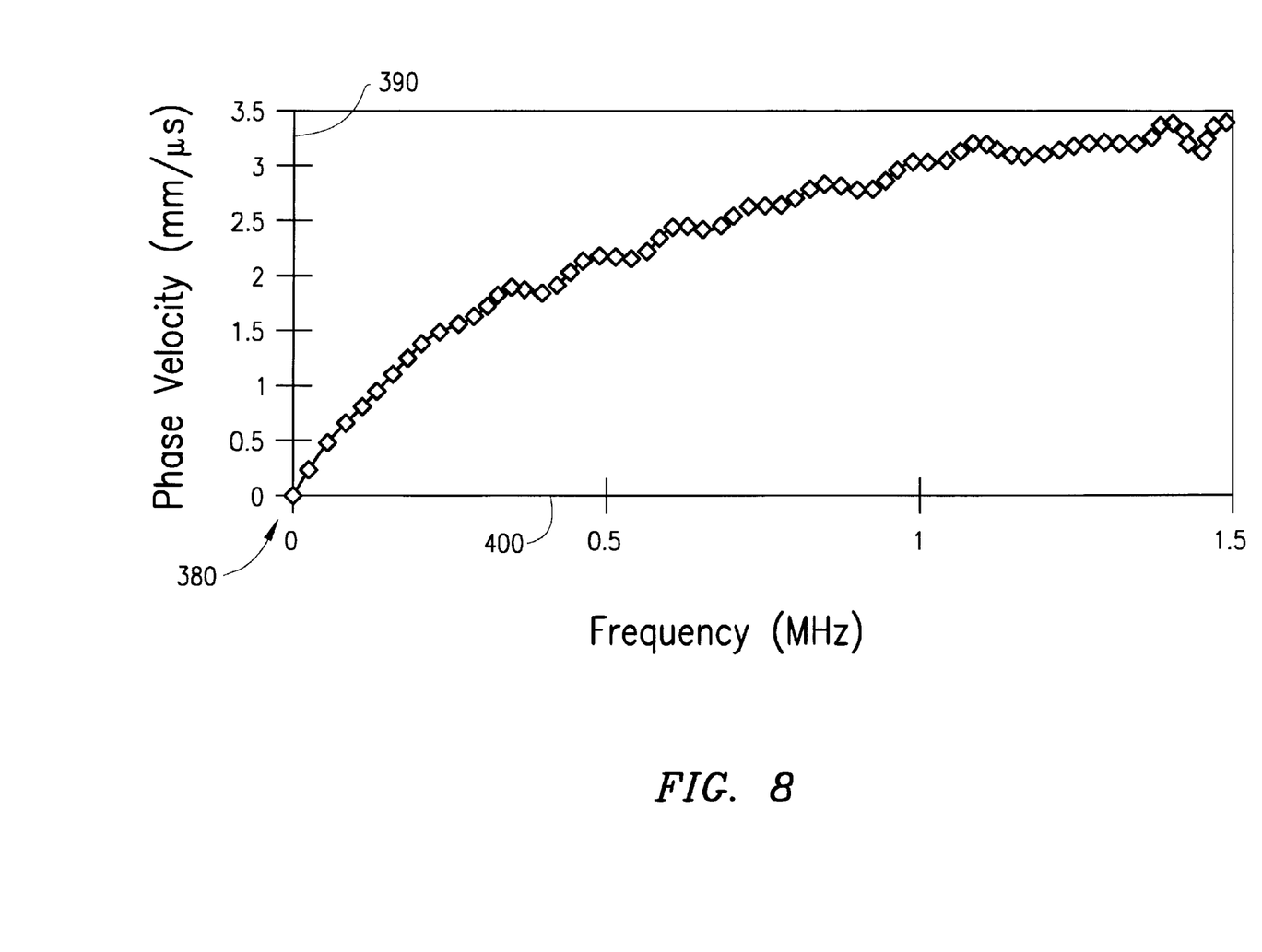
FIG. 8 is a phase velocity graph for detected ultrasound waves at a fixed temperature in a semiconductor wafer.

Several techniques are available to measure the velocity of dispersive waves. If frequency domain analysis is chosen, the phase of each signal is calculated and the velocity of each frequency can be determined by the following formula:

$$V(ph) = \frac{2\pi f d}{\Delta \Phi}$$

where f represents the frequency, d is the separation distance between the detection points (290), and $\Delta\Phi$ is the change in phase at the selected frequency f. This method produces accurate results with minimal processing. Other methods, such as using band-pass filters and modifications of the time-of-flight technique, are also available. If frequency domain analysis is chosen, the ultrasound modulated wafer temperature signal (160) can be transformed using commercially available signal processing packages using, for example, the Fourier transform. The phase of the signal can then be extracted from the resulting transformation. Of course, each detection point (290) will provide a waveform having a different phase, since the propagation distance is different for each detection point. As illustrated, each detection point is located approximately 1 mm farther from the generation point (270) than the previous detection point (290). Experimental results indicate that the change in phase for each waveform acquired at various detection points (290) is uniform at a given frequency, as long as the only variable is distance traveled. The phase velocity can be calculated using the equation above, and FIG. 8 illustrates a velocity versus frequency graph for detected ultrasound waves at a fixed temperature in a semi-conductor wafer (180). The velocity axis (390) is measured in terms of millimeters/microseconds and the frequency axis (400) is measured in terms of MHz. The phase velocity signals (410) produce a fairly smooth curve in the figure.

Figure 9:
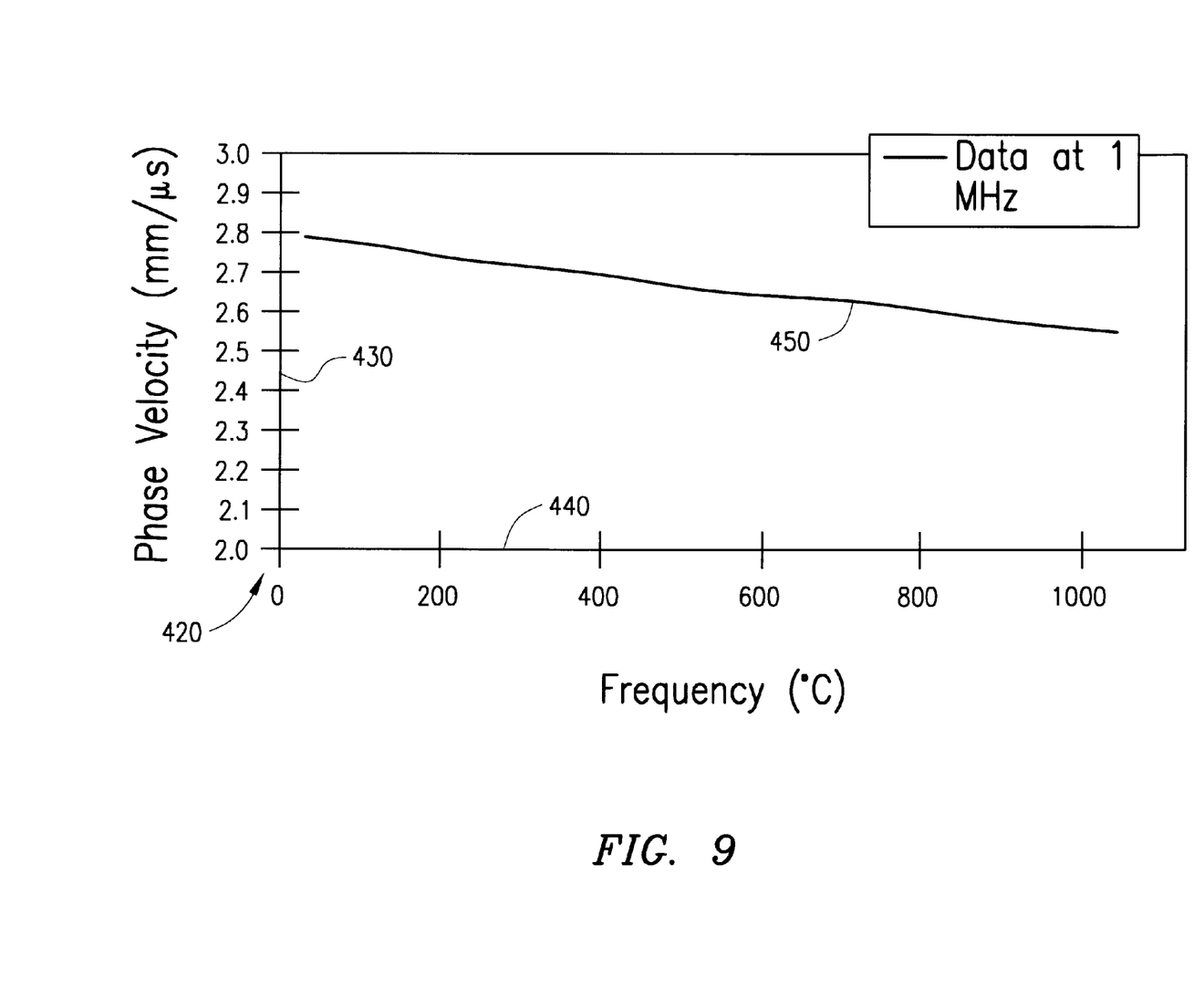
FIG. 9 is a phase velocity graph for detected ultrasound waves at a fixed frequency in a semiconductor wafer.

The phase velocity at each frequency decreases as the temperature of the wafer (180) is increased. This relationship is linear, and is therefore quite useful for wafer (180) temperature measurement. FIG. 9 illustrates a phase velocity graph for detected ultrasound waves at a fixed frequency in a semi-conductor wafer (180). In this case, the velocity versus temperature graph (420) illustrates phase velocity signals (450) at a frequency of 1 MHz. The velocity axis (430) is measured in terms of millimeters/microseconds, while the temperature axis is measured in terms of degrees C. Similar curves are apparent at other frequencies. It has been experimentally determined that averaging the phase velocity measurements over several frequencies that comprise a particular Lamb wave provides better accuracy. For the wafer composition used to produce the data of FIG. 9, a slope of 0.33 mm/$\mu$sec/° C. was obtained. Similar relationships exist for other wafer compositions and geometries.

Narrow band ultrasound generation can also be applied to the detection and control of process temperatures for semiconductor wafers, as mentioned above. When the wavelength is known, the phase velocity may be calculated using the relationship:

$$V(f) = \lambda *$$

where f is obtained from the peak frequency in the spectrum of the narrow band ultrasound generation resulting from particular wavelength reinforcement, and $\lambda$ is the wavelength determined according to the spacing of generation points (270). By varying the wavelength reinforcement frequency, a dispersion curve can be constructed which yields additional information about the wafer characteristics. As mentioned previously, narrow band ultrasound generation is robust, providing a greater signal-to-noise ratio than is available with a single beam, and further, such generation can be easily automated.

Figure 10:
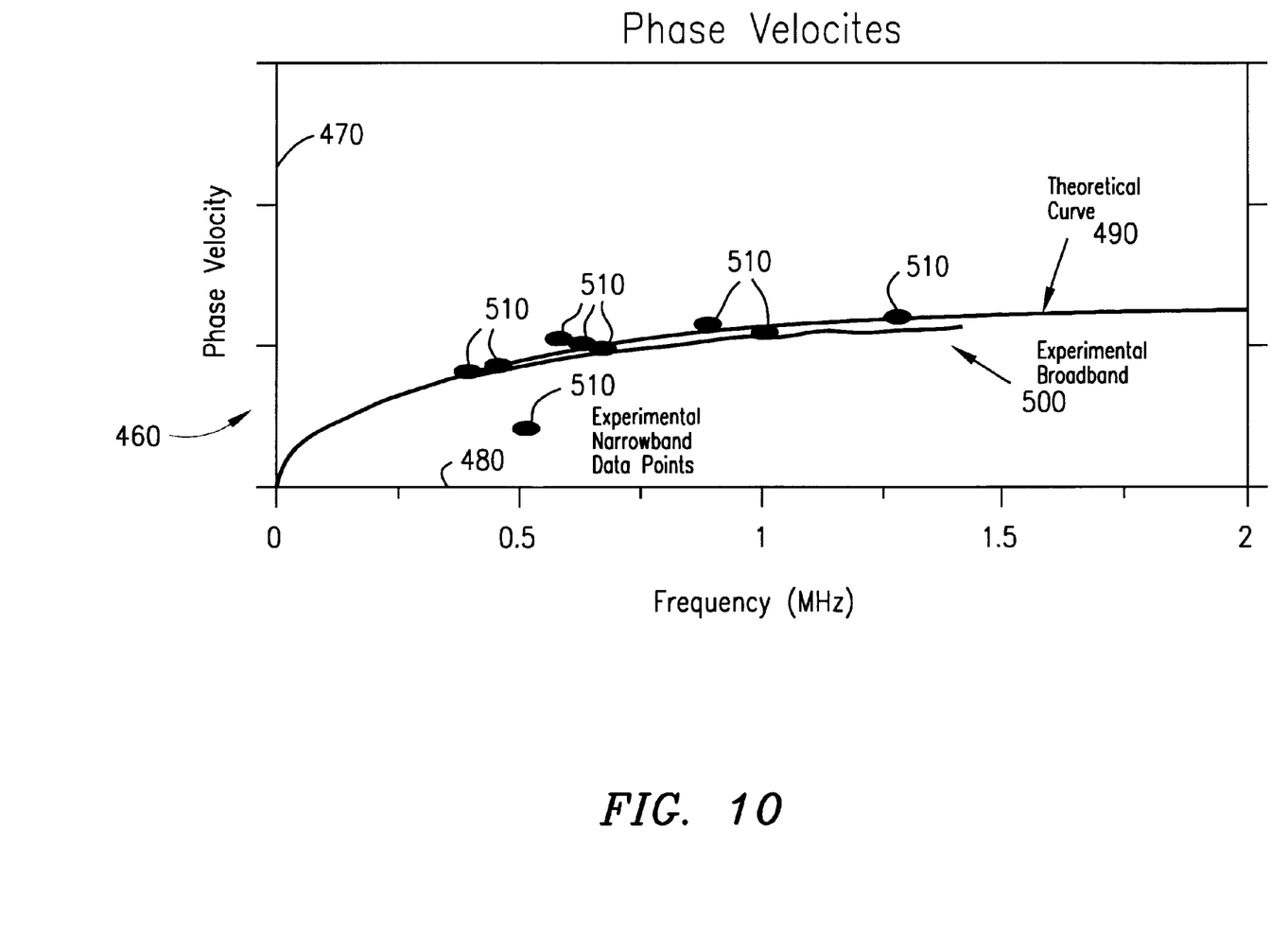
FIG. 10 illustrates a Lamb wave dispersion curve over a range of frequencies in a semiconductor wafer.

FIG. 10 illustrates a Lamb wave dispersion curve over a range of frequencies in a semiconductor wafer (180). This curve may be developed using broad band or narrow band signal generation. As shown in FIG. 10, the phase velocity versus frequency graph (460) indicates that experimental narrow band data points (510), and experimental broad band phase velocity data (500) correlate closely with the theoretically-predicted curve (490). This occurs over a wide frequency range, as shown by the frequency axis (480) which is measured in MHz, and the phase velocity axis (470), which is measured in arbitrary units. Similar phase velocity curves can be obtained for each temperature at which measurements are required. The phase velocity of all frequencies decreases as the temperature of the wafer is increased. This relationship is generally linear, and thus can be used to measure the temperature of the wafer. By following this analysis procedure for Lamb waves sensed and acquired across the entire temperature range of the process, the temperature dependence versus velocity of ultrasound waves within any particular wafer (180) can be determined.

Although the invention has been described with reference to specific embodiments and methods, this description is not meant to be construed in a limited sense. The various modifications of the disclosed embodiments and methods, as well as alternative embodiments and methods of the invention will become apparent to persons skilled in the art upon reference to the description of the invention. It is, therefore, contemplated that appended claims will cover such modifications not filed within the scope of the invention, or their equivalence.

What is claimed is:

1. A system for controlling process temperatures for a semiconductor wafer, comprising:
   a means to heat the wafer;
   a means for generating a plurality of ultrasonic vibrations in the wafer;
   a Sagnac interferometer adapted to sense the plurality of ultrasonic vibrations and generate a wafer temperature signal in response thereto;
   a means to calculate the wafer temperature on the basis of the generated wafer temperature signal from the Sagnac interferometer; and
   a means to control the wafer heating means on the basis of the calculated wafer temperature.

2. The system of claim 1, wherein the means to heat the wafer is a resistance heater.

3. The system of claim 1, wherein the means to heat the wafer is a light bulb.

4. The system of claim 1, wherein the means for generating a plurality of ultrasonic vibrations in the wafer is a linear array of monochromatic light sources.

5. The system of claim 4, wherein the plurality of ultrasonic vibrations comprises Lamb waves.

6. The system of claim 1, wherein the Sagnac interferometer is a polarimetric Sagnac interferometer.

7. The system of claim 1, wherein the wafer temperature signal is correlated to the phase velocity of Lamb waves propagating within the wafer.

8. The system of claim 1, wherein the wafer temperature signal is an ultrasound modulated wafer temperature signal.

9. The system of claim 1, wherein the means to calculate the wafer temperature is an embedded microprocessor.

10. The system of claim 1, wherein the means to control the wafer heating means is a proportional, integral, derivative controller.

11. A method for controlling process temperatures for a semiconductor wafer, comprising the steps of:

heating the wafer;

generating a plurality of ultrasonic vibrations in the wafer;

sensing the plurality of ultrasonic vibrations with a Sagnac interferometer;

generating a wafer temperature signal in response to sensing the plurality of ultrasonic vibrations;

calculating the wafer temperature on the basis of the generated wafer temperature signal from the Sagnac interferometer; and controlling the heat applied to the wafer on the basis of the calculated wafer temperature.

12. The method of claim 11, wherein the step of heating the wafer is carried out using heat provided by a resistance heater.

13. The method of claim 11, wherein the step of heating the wafer is carried out using heat provided by a light bulb.

14. The method of claim 11, wherein the step of generating the plurality of ultrasonic vibrations includes the step of directing light from a linear array of monochromatic light sources to the wafer.

15. The method of claim 14, wherein the step of generating the plurality of ultrasonic vibrations includes the step of generating Lamb waves within the wafer.

16. The method of claim 11, wherein the step of sensing the plurality of ultrasonic vibrations with a Sagnac interferometer includes the step of sensing the plurality of ultrasonic vibrations with a polarimetric Sagnac interferometer.

17. The method of claim 11, wherein the step of generating a wafer temperature signal in response to the plurality of ultrasonic vibrations includes the step of measuring characteristics of Lamb waves traveling within the wafer.

18. The method of claim 11, wherein the step of calculating the wafer temperature on the basis of the generated wafer temperature signal is carried out using an embedded microprocessor.

19. The method of claim 11, wherein the plurality of ultrasonic vibrations comprise Lamb waves having several frequencies, and wherein the step of calculating the wafer temperature on the basis of the generated wafer temperature signal is carried out by averaging phase velocity measurements over the several frequencies.

20. The method of claim 11, wherein the step of controlling the heat applied to the wafer on the basis of the calculated wafer temperature is carried out by a proportional, integral, derivative controller.

* * * * *